(12) United States Patent  (10) Patent No.: US 8,558,039 B2
Sawant et al.  (45) Date of Patent: Oct. 15, 2013

(54) HYDROCARBON FEED FLEXIBLE HIGH PRESSURE NITRATION PLANT DESIGN

(75) Inventors: Mahesh Sawant, Pune (IN); Daniel M. Trauth, Crystal Lake, IL (US); John G. Pendergast, Jr., Lake Jackson, TX (US); Ravindra S. Dixit, Lake Jackson, TX (US)

(73) Assignees: Dow Global Technologies LLC, Midland, MI (US); ANGUS Chemical Company, Buffalo Grove, IL (US)

( * ) Notice: Subject to any disclaimer, the term of this patent is extended or adjusted under 35 U.S.C. 154(b) by 304 days.

(21) Appl. No.: 12/951,800

(22) Filed: Nov. 22, 2010

(65) Prior Publication Data

US 2011/0160496 A1  Jun. 30, 2011

(30) Foreign Application Priority Data

Dec. 24, 2009  (IN) .......................... 3187/CHE/2009

(51) Int. Cl.
*C07C 205/00*  (2006.01)

(52) U.S. Cl.
USPC ......................................... 568/947; 568/948

(58) Field of Classification Search
USPC ................................................ 568/947, 948
See application file for complete search history.

(56) References Cited

U.S. PATENT DOCUMENTS

| | | |
|---|---|---|
| 1,967,667 A | 7/1934 | Hass et al. |
| 2,343,534 A | 3/1944 | Cavanaugh et al. |
| 2,418,241 A | 4/1947 | Stengel et al. |
| 2,455,425 A | 12/1948 | Levy et al. |
| 2,465,959 A | 3/1949 | Tindall |
| 2,489,320 A | 11/1949 | Nygaard et al. |
| 2,491,919 A | 12/1949 | Egly |
| 2,511,454 A | 6/1950 | Bishop et al. |
| 2,512,587 A | 6/1950 | Stengel |
| 2,575,855 A | 11/1951 | Stengel et al. |
| 2,654,658 A | 10/1953 | Marshall |
| 2,654,788 A | 10/1953 | Marshall |
| 2,789,136 A | 4/1957 | O'Hara |
| 2,844,634 A | 7/1958 | McKinnis |
| 3,035,100 A | 5/1962 | Kirby et al. |
| 3,133,124 A | 5/1964 | Bonfield |
| 3,173,961 A | 3/1965 | Drimus et al. |
| 3,657,364 A | 4/1972 | Crawford et al. |
| 3,869,253 A | 3/1975 | L'honore et al. |
| 3,917,705 A | 11/1975 | Swanson et al. |
| 4,313,009 A | 1/1982 | Lhonore et al. |

(Continued)

FOREIGN PATENT DOCUMENTS

| | | |
|---|---|---|
| EP | 0151074 A2 | 8/1985 |
| EP | 0171052 A2 | 2/1986 |

(Continued)

OTHER PUBLICATIONS

PCT Written Opinion of the International Preliminary Examining Authority, PCT International Application No. PCT/US2010/057628, mailed Feb. 14, 2012.

(Continued)

*Primary Examiner* — Jafar Parsa
(74) *Attorney, Agent, or Firm* — McDonnell Boehnen Hulbert & Berghoff LLP

(57) ABSTRACT

Disclosed is an apparatus for synthesizing nitroalkanes by reaction of a hydrocarbon feedstock with aqueous nitric acid. The apparatus may be designed such that it can synthesize more than one nitroalkane using the same equipment.

7 Claims, 5 Drawing Sheets

(56) References Cited

U.S. PATENT DOCUMENTS

| | | | |
|---|---|---|---|
| 4,329,523 | A | 5/1982 | James et al. |
| 4,394,220 | A | 7/1983 | Egly et al. |
| 4,458,094 | A | 7/1984 | Sherwin |
| 4,476,336 | A | 10/1984 | Sherwin |
| 4,518,811 | A | 5/1985 | Lhonore et al. |
| 4,626,607 | A | 12/1986 | Jacquinot et al. |
| 2011/0028731 | A1 | 2/2011 | Trauth et al. |
| 2011/0028732 | A1 | 2/2011 | Trauth et al. |
| 2011/0092737 | A1 | 4/2011 | Trauth |
| 2011/0092748 | A1 | 4/2011 | Sawant et al. |
| 2011/0092749 | A1 | 4/2011 | Sawant et al. |
| 2011/0092750 | A1 | 4/2011 | Trauth et al. |

FOREIGN PATENT DOCUMENTS

| | | |
|---|---|---|
| GB | 916954 | 1/1963 |
| WO | WO2009129099 | 10/2009 |
| WO | WO2011049681 | 4/2011 |
| WO | WO2011049682 | 4/2011 |
| WO | WO2011049683 | 4/2011 |
| WO | WO2011078931 | 6/2011 |

OTHER PUBLICATIONS

PCT International Search Report and Written Opinion, PCT International Application No. PCT/US2010/057628, mailed Mar. 31, 2011.
PCT Written Opinion of the International Preliminary Examining Authority, PCT International Application No. PCT/US2010/048482, mailed Oct. 18, 2011.
PCT International Preliminary Report on Patentability, PCT International Application No. PCT/US2010/048482, mailed Jan. 24, 2012.
PCT International Search Report and PCT Written Opinion, PCT International Application No. PCT/US2010/048482, mailed Nov. 17, 2010.
Albright, Lyle F., Nitration of Paraffins, Chemical Engineering, Jun. 6, 1966, pp. 149-156.
Olujic Z. et al., "Equipment improvement trend in distillation", Chemical Engineering and Processing, vol. 48, Mar. 26, 2009, pp. 1089-1104.
PCT Written Opinion of the International Preliminary Examining Authority, PCT International Application No. PCT/US2010/048487, mailed Oct. 18, 2011.
PCT International Preliminary Report on Patentability, PCT International Application No. PCT/US2010/048487, mailed Feb. 20, 2012.
PCT International Search Report, PCT International Application No. PCT/US2010/048487, mailed Feb. 28, 2011.
PCT International Preliminary Report on Patentability, PCT International Application No. PCT/US201048480, mailed May 3, 2012.
PCT International Search Report and PCT Written Opinion, PCT International Application No. PCT/US2010048480, mailed Mar. 2, 2011.
PCT International Preliminary Report on Patentability, PCT International Application No. PCT/US2010/057628, mailed Jul. 6, 2012.
PCT Written Opinion of the International Preliminary Examining Authority, PCT International Application No. PCT/US2010/057628, mailed Apr. 4, 2012.
Reply to Written Opinion, PCT International Application No. PCT/US2010/048482, filed Aug. 16, 2011.
Reply to Written Opinion, PCT International Application No. PCT/US2010/048487, filed Aug. 16, 2011.
Reply to Written Opinion, PCT International Application No. PCT/US2010/057628, filed Oct. 19, 2011.
Office Action, U.S. Appl. No. 12/879,799, mailed Aug. 30, 2012.
PCT International Search Report and Written Opinion, PCT International Application No. PCT/US2010/048487, mailed Feb. 28, 2011.
Office Action, U.S. Office U.S. Appl. No. 12/879,824, mailed Sep. 21, 2012.
Chinese Patent Application No. 201080061242.1, Office Action and Search Report, Aug. 5, 2013.

HYDROCARBON FEED FLEXIBLE HIGH PRESSURE NITRATION PLANT DESIGN

CROSS-REFERENCE TO RELATED APPLICATIONS

This application claims priority to Indian Provisional Application No. 3187/CHE/2009, filed Dec. 24, 2009, which is hereby incorporated herein by reference in its entirety.

FIELD

This invention relates to nitroalkane synthesis and, more particularly, to methods and apparatuses for synthesizing different nitroalkanes from different hydrocarbon feedstocks using the same equipment.

BACKGROUND

High pressure nitration is a highly selective process, which allows for the production of a wide range of specialty chemicals. However, high pressure nitration is complex and capital intensive. Typically, different chemical plants or individual batch processes must be used in order to nitrate different compounds. High pressure nitration requires many pieces of expensive equipment, such as absorbers and stripping apparatuses. A need exists, therefore, for simplified, flexible, and economical processes and apparatuses for the manufacture of a variety of nitrated compounds.

BRIEF SUMMARY

In one aspect, an illustrative embodiment provides an apparatus for selectively synthesizing at least a first nitroalkane using a first feedstock and at least a second nitroalkane using a second feedstock, wherein the first feedstock comprises a first hydrocarbon and the second feedstock comprises a second, different hydrocarbon. The apparatus comprises a reactor for selectively reacting the first feedstock and the second feedstock with aqueous nitric acid to product a reaction product stream, wherein the reaction product stream comprises the first nitroalkane when the first feedstock is used and comprises the second nitroalkane when the second feedstock is used. The apparatus further comprises a separating system for forming a gas-recovered aqueous phase and a gas-recovered oil phase from the reaction product stream and a recovery system for recovering the first nitroalkane from at least one of the gas-recovered aqueous phase and the gas-recovered oil phase when the first feedstock is used and for recovering the second nitroalkane from at least one of the gas-recovered aqueous phase and the gas-recovered oil phase when the second feedstock is used.

In another aspect, an illustrative embodiment provides a process for synthesizing a first nitroalkane and a second nitroalkane. The process comprises: reacting a first feedstock in a reactor with aqueous nitric acid to produce a first reaction product stream; quenching the first reaction product stream in a cooling system such that it phase separates into at least a first gas phase, a first oil phase, and a first aqueous phase; absorbing in an absorber water-soluble and oil-soluble components from the first gas phase to form a first hydrocarbon gas stream and a first gas-recovered mixture; forming in a separator a first combined gas-recovered aqueous phase and a first combined gas-recovered oil phase from the first gas-recovered mixture, the first oil phase, and the first aqueous phase; and recovering in the first nitroalkane from at least one of the first combined gas-recovered aqueous phase and the first combined gas-recovered oil phase. The process further comprises: reacting a second feedstock in the reactor with aqueous nitric acid to produce a second reaction product stream; quenching the second reaction product stream in the cooling system such that it phase separates into at least a second gas phase, a second oil phase, and a second aqueous phase; absorbing in the absorber water-soluble and oil-soluble components from the second gas phase to form a second hydrocarbon gas stream and a second gas-recovered mixture; forming in the separator a second combined gas-recovered aqueous phase and a second combined gas-recovered oil phase from the second gas-recovered mixture, the second oil phase, and the second aqueous phase; and recovering the second nitroalkane from at least one of the second combined gas-recovered aqueous phase and the second combined gas-recovered oil phase.

In yet another aspect, an illustrative embodiment provides an apparatus for selectively synthesizing at least a first nitroalkane using a first feedstock and at least a second nitroalkane using a second feedstock, wherein the first feedstock comprises a first hydrocarbon and the second feedstock comprises a second, different hydrocarbon. The apparatus comprises a reactor for selectively reacting the first feedstock and the second feedstock with aqueous nitric acid to product a reaction product stream, wherein the reaction product stream comprises the first nitroalkane when the first feedstock is used and comprises the second nitroalkane when the second feedstock is used. The apparatus further comprises a cooling system for quenching the reaction product stream such that it phase separates into at least a gas phase, an oil phase, and an aqueous phase; an absorber for absorbing water-soluble and oil-soluble components from the gas phase to form a gas-recovered mixture; a stripper for removing dissolved organic compounds from the gas-recovered mixture to form a stripped gas-recovered mixture; a separator for forming a combined gas-recovered aqueous phase and a combined gas-recovered oil phase from the stripped gas-recovered mixture, the oil phase, and the aqueous phase; and a recovery system for recovering the first nitroalkane from at least one of the combined gas-recovered aqueous phase and the combined gas-recovered oil phase when the first feedstock is used and for recovering the second nitroalkane from at least one of the gas-recovered aqueous phase and the gas-recovered oil phase when the second feedstock is used.

The foregoing summary is illustrative only and is not intended to be in any way limiting. In addition to the illustrative aspects, embodiments, and features described above, further aspects, embodiments, and features will become apparent by reference to the drawings and the following detailed description.

DETAILED DESCRIPTION

In one aspect, an apparatus for selectively synthesizing at least a first nitroalkane using a first feedstock and at least a second nitroalkane using a second feedstock is provided. Thus, the apparatus may be flexible enough to synthesize different nitroalkanes using the same equipment. The different nitroalkanes that may be synthesized in this way include two or more of the following: 2-nitropropane, nitrocyclohexane, tert-nitrobutane, and nitro-n-octane.

Figure 1:
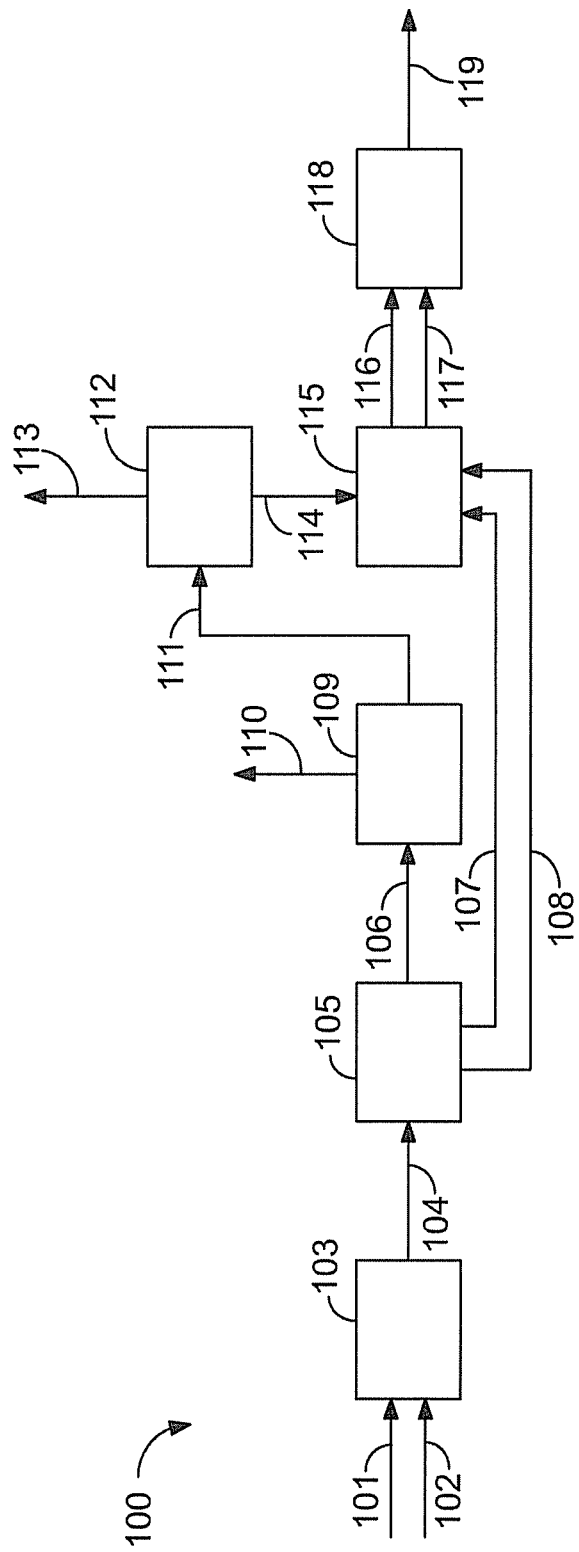
FIG. 1 is a schematic diagram of an apparatus for synthesizing nitroalkanes, in accordance with an illustrative embodiment.

FIG. 1 illustrates an apparatus 100 for selectively synthesizing at least a first nitroalkane using a first feedstock and at least a second nitroalkane using a second feedstock. A hydrocarbon feedstock 101 and aqueous nitric acid 102 may be introduced into a reactor 103. The hydrocarbon feedstock 101 may be a first feedstock comprising a first hydrocarbon or a second feedstock comprising a second, different hydrocarbon. For example, the hydrocarbon feedstock may include, without limitation, propane, cyclohexane, isobutane, or n-octane. The hydrocarbon feedstock 101 and the aqueous nitric acid 102 may react at a reactor pressure and a reaction temperature, such that a reaction product stream 104 comprising nitrated compounds and byproducts may be formed. The reaction product stream 104 may comprise the first nitroalkane when the first feedstock is used and may comprise the second nitroalkane when the second feedstock is used. For example, when the hydrocarbon feedstock 101 comprises propane, the reaction product stream 104 may include nitropropane. When the hydrocarbon feedstock 101 comprises cyclohexane, the reaction product stream 104 may include nitrocyclohexane. When the hydrocarbon feedstock 101 comprises isobutane, the reaction product stream 104 may include tert-nitrobutane. When the hydrocarbon feedstock 101 comprises n-octane, the reaction product stream may include nitro-n-octane.

The hydrocarbon feedstock 101 and the aqueous nitric acid 102 may be mixed, or partially mixed, prior to entry into the reactor 103, or alternatively; they may be added individually, with mixing to occur within the reactor 103. In addition, the hydrocarbon feedstock 101 and the aqueous nitric acid 102, whether added together or individually, may be preheated prior to entry into the reactor 103.

The aqueous nitric acid 102 may be delivered to the reactor 103 in the form of an aqueous solution that contains at least about 10 weight percent, preferably at least about 15 weight percent, more preferably at least about 20 weight percent, of the acid. Further, the solution may contain less than about 50 weight percent, preferably less than about 40 weight percent, and more preferably less than about 35 weight percent, of the acid. In other embodiments, the nitric acid solution may contain between about 15 and about 40 weight percent of the acid. In further embodiments, the nitric acid solution may contain between about 18 and about 35 weight of the acid.

The mole ratio of the hydrocarbon feedstock 101 to the aqueous nitric acid 102 may be at least about 0.3:1, more preferably at least about 0.5:1.

The reactor pressure may be at least about 500 psi (34 atm), more preferably at least about 1000 psi (68 atm), and further preferably at least about 1200 psi (82 atm). In some embodiments, the pressure may be about 1600 psi (109 atm) or less, preferably about 1500 psi (102 atm) or less, more preferably about 1400 psi (95 atm) or less. In other embodiments, the pressure may between about 1000 psi (68 atm) and 1400 psi (95 atm). Various methods known in the art may be used for maintaining the pressure within the desired range including, for example, through the use of a back-pressure regulator.

The reaction temperature within the reactor may be controlled (for example with heat exchange fluid or using heat generated from the reaction) to at least about 140 degrees Celsius and to less than about 325 degrees Celsius. In other embodiments, the temperature may be at least about 215 degrees Celsius and to less than about 325 degrees Celsius. In some embodiments, the temperature may be at least about 180 degrees, at least about 200 degrees, at least about 230 degrees, or at least about 240 degrees. In other embodiments, the temperature may be less than about 290 degrees, less than about 280 degrees, less than about 270 degrees, or less than about 250 degrees. In further embodiments, the temperature may be between about 200 and 250 degrees Celsius. In yet further embodiments, the temperature may be between about 215 and 280 degrees Celsius, or between about 220 and 270 degrees Celsius.

The residence time of the reactants in the reactor 103 may be preferably at least about 30 seconds, more preferably at least about 90 seconds. Residence time may be controlled in various ways including, for example, by the length and/or width of the reactor or through the use of packing material. Residence time may be determined by dividing the volume of the reactor by the inlet flow rates.

The reactor 103 may be a downflow configured reactor. That is, the reactor, which is preferably of an elongated and linear shape, such as a tube shape, may be positioned so that reactants are added through an entry port at or near the top of the reactor and then flow down the reactor for a residence time that is sufficient to allow reaction to occur and formation of the desired product. The product mixture may be collected through an exit port at or near the bottom of the reactor.

The operation of the reactor in a downflow configuration provides certain advantages over prior art systems, which generally utilize a horizontal, upflow, coiled or a batch autoclave type apparatus. In particular, the downflow configuration of the invention provides nitrated compounds that contain relatively low levels of oxidation byproducts as compared to such prior art systems.

Without wishing to be bound by any particular theory, it is believed that the advantages of the downflow reactor result primarily from its ability to minimize the amount and residence time of the liquid phase within the reactor. The liquid phase in general contains a low mole ratio of hydrocarbons to nitric acid. This low mole ratio favors oxidation chemistry at the expense of nitration and oxidation therefore primarily occurs in the liquid phase. In a downflow reactor (also referred to as a trickle bed reactor) the gas is the continuous phase and the liquid trickles down the reactor walls or packing. Therefore, the amount of liquid phase(s) in a downflow configured reactor is maintained at a low level and consequently oxidation chemistry is minimized.

In contrast, in an upflow reactor, also referred to as a bubble column, the liquid is the continuous phase (and bubbles rise quickly through the continuous liquid phase). Thus, an upflow reactor maximizes the liquid holdup. Because, as noted above, oxidation primarily occurs in the liquid phase, the upflow reactor maximizes the formation of oxidation byproducts. Similarly, coil and horizontal reactor configurations also increase liquid residence time and therefore oxidation chemistry as compared to a downflow reactor. A further disadvantage of coiled reactors is that they are not well-suited for industrial scale production because of the difficulty of fabricating large scale reactors in this shape.

The reactor 103 may also be packed with a packing material to improve reactant mixing and heat transfer and/or to vary the reactor volume. Packing of the reactor may be preferred, for example, in a propane nitration system where it is desired to increase the concentration of 2,2-dinitropropane in the reaction product stream. Suitable packing materials may include, for example, glass beads, random packing, or structured packing, such as those typically employed in distillation devices. Other packing materials are known in the art and may be used. The reactor 103 may also be an un-packed reactor.

The reaction product stream 104 then may enter a cooling system 105. The cooling system 105 may be, for example, a three-phase flash vessel. In the cooling system 105, the reaction product stream 104 may be quenched such that it separates into at least a gas phase 106, an oil phase 107, and an aqueous phase 108. One or more of the gas phase 106, the oil phase 107, and the aqueous phase 108 may contain nitrated compounds.

The gas phase 106 may enter an absorber 109 for absorbing water-soluble and oil-soluble components from the gas phase 106 to form a first hydrocarbon gas stream 110 and a gas-recovered mixture 111. The absorber 109 may use fresh or recycled water to absorb the water-soluble and oil-soluble components from the gas phase 106.

The gas-recovered mixture 111 may then enter a stripping apparatus 112, where dissolved organic compounds may be released as a second hydrocarbon gas stream 113, resulting in a stripped gas-recovered mixture 114. The stripped gas-recovered mixture 114, the oil phase 107, and the aqueous phase 108 may enter a separator 115, for forming a combined gas-recovered aqueous phase 116 and a combined gas-recovered oil phase 117 from the stripped gas-recovered mixture 114, the oil phase 107, and the aqueous phase 108. For example, water-soluble portions of the stripped gas-recovered mixture 114 may combine with the aqueous phase 108 to form the combined gas-recovered aqueous phase 116 and oil soluble portions of the stripped gas-recovered mixture 114 may combine with the oil phase 107 to form the combined gas-recovered oil phase 117.

The combined gas-recovered aqueous phase 116 and/or the combined gas-recovered oil phase 117 may then enter a recovery system 118 for recovering a nitroalkane 119. The nitroalkane 119 may be recovered from either the combined gas-recovered oil phase 117 or the combined gas-recovered aqueous phase 116 or both. The recovery system 118 may include at least one stripping apparatus. The recovery system 118 may also include, among other elements, a nitroalkane recovery section, which may include a plurality of columns for recovering the desired nitroalkane, a neutralizer for neutralizing organic acids in the oil phase 107, and a Karr® column for water-washing a neutralized oil stream. When the hydrocarbon feedstock 101 comprises the first hydrocarbon, the nitroalkane 119 may be the first nitroalkane. When the hydrocarbon feedstock 101 comprises the second hydrocarbon, the nitroalkane 119 may be the second nitroalkane.

In an illustrative embodiment, a first hydrocarbon feedstock may comprise propane and a first nitroalkane may be 2-nitropropane and a second hydrocarbon feedstock may comprise isobutane and a second nitroalkane may be tert-nitrobutane. In another illustrative embodiment, a first hydrocarbon feedstock may comprise cyclohexane and a first nitroalkane may be nitrocyclohexane and a second hydrocarbon feedstock may comprise n-octane and a second nitroalkane may be nitro-n-octane.

In an illustrative embodiment, a third nitroalkane may also be synthesized using a third feedstock. The third feedstock may include a third hydrocarbon that is different from the first hydrocarbon and the second hydrocarbon. In another illustrative embodiment, a fourth nitroalkane may also be synthesized using a fourth feedstock. The fourth feedstock may include a fourth hydrocarbon that is different from the first hydrocarbon, the second hydrocarbon, and the third hydrocarbon.

According to one embodiment, propane is reacted with aqueous nitric acid to form 2-nitropropane and other nitrated paraffins under the specific process conditions described herein. The reaction of propane with nitric acid may be carried out in a corrosion resistant reactor, such as a titanium reactor. The reactor is optionally surrounded by a shell with input and output ports for feeding a heat transfer fluid to the reactor. The heat transfer fluid, which can be, for example, an oil, allows the temperature of the reaction to be controlled to within the desired parameters.

It should be noted, however, that because the reaction between the nitric acid and propane is exothermic, use of a shell and a heat transfer fluid are not required. The temperature of the reaction can be regulated to be within the desired parameters by simply regulating the addition rate and/or concentration of the reactants.

EXAMPLES

Various examples are demonstrated using a computer simulation. The design bases in Tables 1-4 are from laboratory runs.

Example 1

Nitration of Propane

Figure 2:
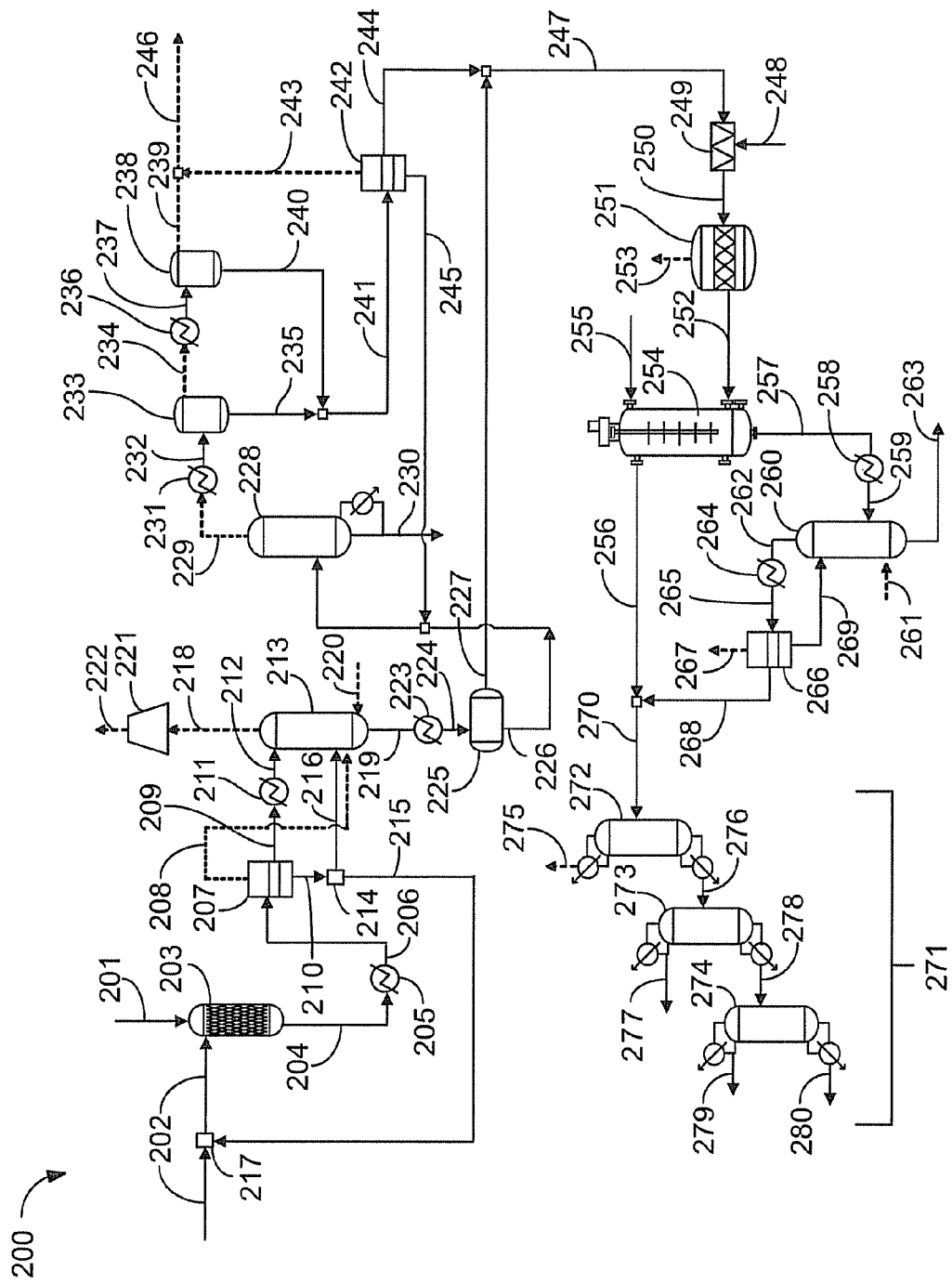
FIG. 2 is a schematic diagram of an apparatus for synthesizing nitropropane, in accordance with an illustrative embodiment.

Propane is nitrated using about 30 weight percent dilute aqueous nitric acid as the nitrating agent at the following process conditions: about 1400 psig reactor pressure, about 230 degrees Celsius reactor temperature, a residence time of about 120 seconds, and a propane to nitric acid mole ratio of about 1.5:1. FIG. 2 illustrates an apparatus 200 for synthesizing nitropropane. A hydrocarbon feedstock 201 comprising propane and aqueous nitric acid 202 are introduced into a reactor 203 and react to form a reaction product stream 204. A composition of a typical reaction product stream 204 from the reactor 203 is summarized in Table 1.

TABLE 1

Reaction product stream composition for propane nitration

| Component | Weight percent | lb/h |
|---|---|---|
| Water | 68.7 | 46517 |
| Carbon monoxide | 0.9 | 613 |
| Nitrogen | 0.5 | 339 |
| Nitric oxide | 3.2 | 2134 |
| Nitrous oxide | 0.7 | 449 |
| Propane | 13.5 | 9173 |
| Carbon dioxide | 1.7 | 1183 |
| Acetone | 0.2 | 117 |
| Acetic acid | 1.8 | 1241 |
| Nitromethane | 0.1 | 62 |
| Nitroethane | 0.1 | 42 |
| Propionic acid | 0.2 | 147 |
| 2-nitropropane | 7.5 | 5064 |
| 1-nitropropane | 0.7 | 460 |
| 2,2-dinitropropane | 0.3 | 215 |

Downstream separation equipment, such as an absorber and a stripping apparatus, is designed based on the concentration and flow rates of the stream coming out of the reactor.

The aqueous recycle propane nitration scheme outlined below is designed on the basis of a production rate of 5064 lb/h of 2-nitropropane. The reaction product stream 204 is cooled in a first condenser 205 to produce a condensed reaction product stream 206, which is a multiphase product stream and which enters a first three-phase flash vessel 207. The first three-phase flash vessel 207 performs a three phase (vapor-liquid-liquid) flash/quench of the condensed reaction product stream 206 and produces a gas phase 208 and two distinct liquid phases—an oil phase 209 (including nitroalkanes) and an aqueous phase 210 (including water and organic acids). The oil phase 209 is cooled to between about 10 and 20 degrees Celsius in a second condenser 211 to produce a condensed oil phase 212 to reduce loss of nitropropanes in the overhead. The condensed oil phase 212 is introduced into an absorber 213. The aqueous phase 210 enters a stream-splitter 214, which splits the aqueous phase 210 into a first aqueous stream 215 and a second aqueous stream 216. The stream-splitter 214 may include at least one flow-meter to control the amount of the aqueous phase 210 in the first aqueous stream 215 and the second aqueous stream 216. The first aqueous stream 215 enters a recycling system 217. The recycling system 217 mixes the first aqueous stream 215 with the aqueous nitric acid 202 such that the first aqueous stream 215 dilutes the aqueous nitric acid 202 prior to entering the reactor 203.

In high pressure propane nitration, it has been successfully demonstrated that 70-80% of the aqueous phase 210 originating from the nitration product quench can be directly recycled back with its dissolved organic acids and nitroalkanes content. This can beneficially result in simplified operation as well as reduced capital and energy intensity.

According to this scheme, approximately 70-80% of the aqueous phase 210 coming out of the post-reactor first three-phase flash vessel 207 is recycled to the reactor 203 as nitric acid diluent. Nitropropanes (2-nitropropane and 1-nitropropane) typically have low solubility in water resulting in a concentration of about 8200 ppm in the aqueous recycle stream. Moreover, nitropropanes are significantly less reactive than propane and therefore their presence in the reactor should not affect reactor performance significantly.

The absorber 213 absorbs water-soluble and oil soluble components from the gas phase 208 into the condensed oil phase 212 and into the second aqueous stream 216 to form a hydrocarbon gas stream 218 and a gas-recovered mixture 219. In the absorber 213, the gas phase 208 is steam stripped with steam 220 of all volatiles at about 41-74 psi (3-5 atm) and the resulting hydrocarbon gas stream 218, which essentially contains un-reacted propane and gas byproducts, is then compressed to about 147 psi (10 atm) in a two-stage compressor 221 before a compressed hydrocarbon gas stream 222 is sent to propane recovery.

The gas-recovered mixture 219 from the absorber 213 is cooled in a third condenser 223 to produce a condensed gas-recovered mixture 224, which is phase-separated in a separator 225 into a gas-recovered aqueous phase 226 and a gas-recovered oil phase 227. In alternative embodiments, the condensed oil phase 212 and the second aqueous stream 216 do not enter the absorber 213 and instead directly enter the separator 225. In such alternative embodiments, the condensed gas-recovered mixture 224 may enter a stripping apparatus for removing dissolved organic compounds prior to entering the separator 225. In the separator 225, a combined gas-recovered aqueous phase and a combined gas-recovered oil phase may be formed from the stripped gas-recovered mixture, the condensed oil phase 212, and the second aqueous stream 216. For example, water-soluble portions of the stripped gas-recovered mixture may combine with the second aqueous stream 216 to form the combined gas-recovered aqueous phase and oil soluble portions of the stripped gas-recovered mixture may combine with the condensed oil phase 212 to form the combined gas-recovered oil phase. Nitropropanes are recovered in a recovery system from both the gas-recovered aqueous phase 226 and the gas-recovered oil phase 227. The gas-recovered aqueous phase 226 is further sent to a first stripping apparatus 228, which is operated at atmospheric pressure to recover dissolved nitropropanes. The first stripping apparatus 228 divides the gas-recovered aqueous stream 226 into a first top product 229 and a first bottom product 230. Water, organic acids, and nitric acid are obtained as the first bottom product 230, whereas the first top product 229 is cooled and separated (decanted) to obtain nitropropanes. The first bottom product 230 is sent to a water treatment section for recovery of organic acids.

The first top product 229 is introduced into a fourth condenser 231 to produce a condensed first top product 232, which is introduced into a first flash pot 233 to provide a second top product 234 and a second bottom product 235. The second top product 234 is then introduced into a fifth condenser 236 to produce a condensed second top product 237, which is then introduced into a second flash pot 238 to provide a third top product 239 and a third bottom product 240. The second bottom product 235 and the third bottom product 240 are combined to form a fourth bottom product 241. The fourth bottom product 241 enters a second three-phase flash vessel 242 to produce a fourth top product 243, a middle product 244, which is predominantly an oil phase, and a fifth bottom product 245, which is predominantly an aqueous phase. The fifth bottom product 245 is recycled back to the gas-recovered aqueous phase 226. The fourth top product 243 combines with the third top product 239 to form a non-condensable stream 246. Compared to a conventional scheme without aqueous recycle, the non-condensable stream 246 is small and contains a negligible amount of propane and 2-nitropropane, thus eliminating the need for a tail-gas recovery column.

The middle product 244 combines with the gas-recovered oil phase 227 to produce a first oil stream 247. The first oil stream 247 contains the recovered nitropropanes along with dissolved organic acids which may need to be removed. Sodium bicarbonate 248 is added to the first oil stream 247 in mixer 249, resulting in a first neutralized oil stream 250. The first neutralized oil stream 250 is then routed to a neutralization tank 251, which is agitated to allow for thorough mixing and degassing of carbon-dioxide released during neutralization. A second neutralized oil stream 252 exits the neutralization tank 251. Carbon-dioxide 253 is vented from the neutralization tank 251 and the second neutralized oil stream 252 (containing dissolved salts) is sent to a Karr® column 254 for washing off the dissolved salts with deionized water 255 to form a washed oil stream 256 and a washed aqueous stream 257. A reciprocating Karr® column is known to be an effective mass transfer device. A Karr® column is an efficient counter-current liquid/liquid extraction device which provides good mass transfer at reasonably high throughput capacities (up to 1500 gal/hr/ft$^2$ or about 60 m$^3$/hr/m$^2$). Karr® columns also allow considerable flexibility of operation, because agitation intensity is easily adjusted and a unit can be operated over a wide range of feed rates without reduction in performance. The washed aqueous stream 257 from the Karr® column 254 contains dissolved nitropropanes which are condensed in a sixth condenser 258 to produce a condensed washed aqueous stream 259, which is sent to a second stripping apparatus 260 to be stripped with steam 261. The second stripping apparatus 260 divides the condensed washed aqueous stream 259 into a fifth top product 262 and a sixth bottom product 263 which is routed to a waste water section. The fifth top product 262 enters a seventh condenser 264, to produce a condensed fifth top product 265. The condensed fifth top product 265 enters a third three-phase flash vessel 266, which separates the condensed fifth top product 265 into a second gas phase 267, a second oil phase 268, and a second aqueous phase 269. The second aqueous phase 269 is returned to the second stripping apparatus 260. The second oil phase 268 is combined with the washed oil stream 256 to form a second oil stream 270, which is routed to a Nitroalkane Recovery Section (NRS) 271.

The NRS consists of three columns, a Combiner Drying-Volatile Removal column (CDVR) 272, a 2-nitropropane column 273, and a 1-nitropropane column 274. The second oil stream 270 enters the CDVR 272 and is stripped of its volatile organic compounds (for example, acetone and butane), water, and the low molecular weight nitroalkanes (for example, nitromethane, and nitroethane), which exit the CDVR 272 in a CDVR top product 275. A CDVR bottom product 276 essentially contains 2-nitropropane, 1-nitropropane, 2,2-dinitropropane, and residual quantities of nitrobutane. The CDVR bottom product 276 is sent to the 2-nitropropane column 273, which essentially recovers essentially pure 2-nitropropane in a first nitroalkane stream 277. A 2-nitropropane bottom product 278 is sent to the 1-nitropropane column 274, which recovers essentially pure 1-nitropropane in a second nitroalkane stream 279 and heavies (such as 2,2-dinitropropane, 1-nitrobutane, and 2-nitrobutane) in a 1-nitropropane column bottom product 280.

Example 2

Nitration of Cyclohexane

In this example, ten cyclohexane nitration runs are carried out using 30% nitric acid and the effect of pressure, reactor temperature, and hydrocarbon to nitric acid mole ratio on yield and conversion is studied. Nitric acid conversions greater than 99% and cyclohexane conversion ranging from 20-40% can be achieved. The co-current downflow reactor designed for propane nitration is highly effective for nitrating cyclohexane.

Next, the hydrocarbon phase is washed with a sodium bicarbonate solution in order to neutralize any acidity. The hydrocarbon phase is neutralized and water-washed before stripping off cyclohexane in order to achieve quick and efficient hydrocarbon/aqueous phase separation.

Oil from the separator is fed to an 80 tray Karr® column with a variable drive unit to adjust mixing intensity. Deionized water is fed near the top of the column while the separated oil is fed near the bottom of the column.

Figure 3:
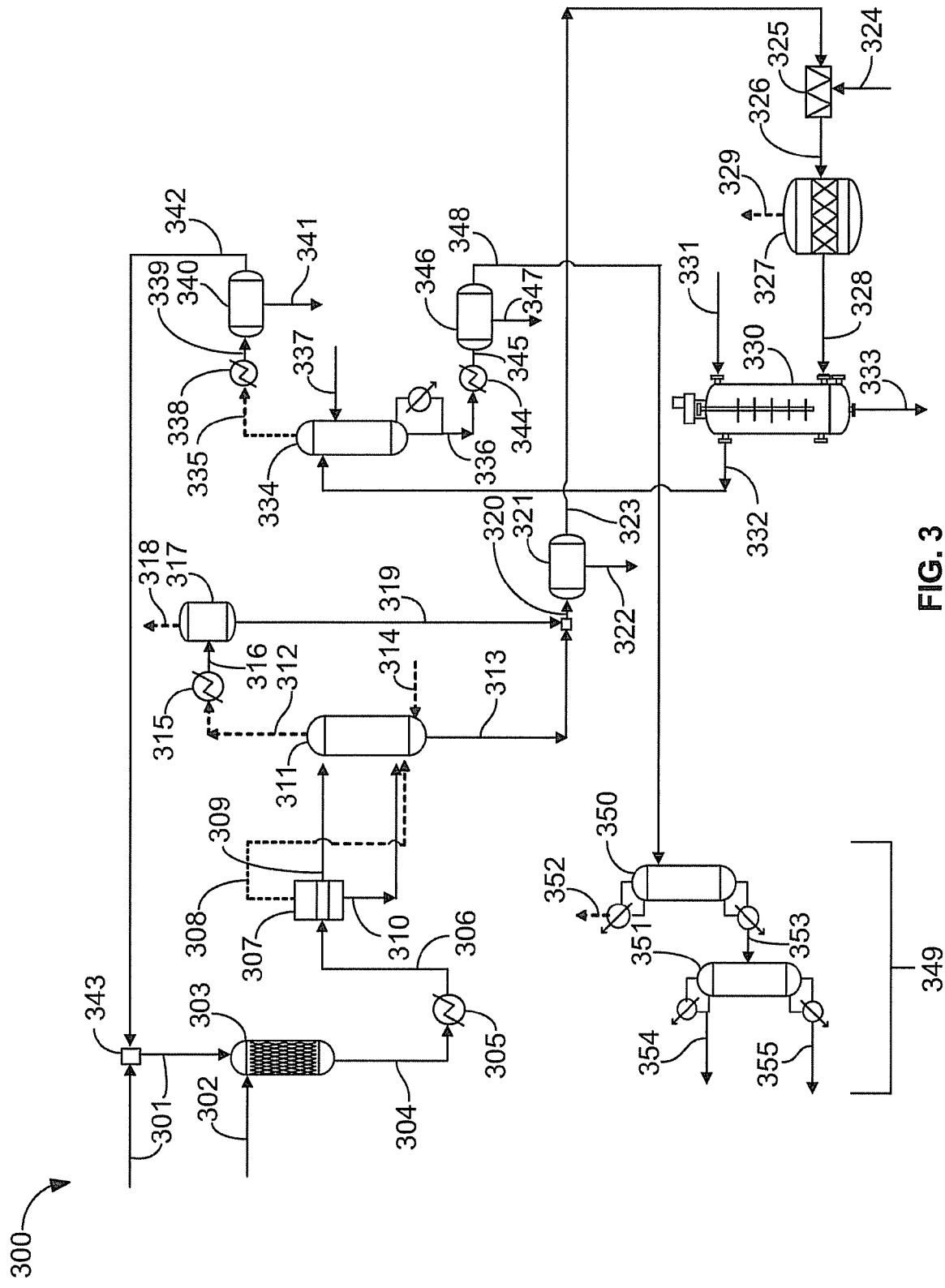
FIG. 3 is a schematic diagram of an apparatus for synthesizing nitrocyclohexane, in accordance with an illustrative embodiment.

Essentially the same manufacturing setup discussed above for propane nitration is used to nitrate cyclohexane and obtain nitrocyclohexane within product purity specifications. Cyclohexane is nitrated using about 30 weight percent dilute aqueous nitric acid as the nitrating agent at the following process conditions: about 1200 psig reactor pressure, about 220 degrees Celsius reactor temperature, a residence time of about 120 seconds, and a cyclohexane to nitric acid mole ratio of about 2:1. FIG. 3 illustrates an apparatus 300 for synthesizing nitrocyclohexane. A hydrocarbon feedstock 301, comprising cyclohexane, and aqueous nitric acid 302 are introduced into a reactor 303 and react to form a reaction product stream 304. A composition of a typical reaction product stream 304 from the reactor 303 is summarized in Table 3.

TABLE 2

Reaction product stream composition for cyclohexane nitration

| Component | Weight percent | lb/h |
|---|---|---|
| Water | 49.2 | 19816 |
| Nitric acid | 0.3 | 108 |
| Cyclohexane | 29.5 | 11875 |
| Cyclohexanol | 0.7 | 270 |
| Nitrocyclohexane | 12.6 | 5064 |
| Succinic acid | 0.5 | 198 |
| Glutaric acid | 0.9 | 372 |
| Adipic acid | 1.5 | 605 |
| Carbon dioxide | 1.9 | 750 |
| Nitrous oxide | 0.7 | 279 |
| Nitric oxide | 1.6 | 627 |
| Nitrogen | 0.5 | 218 |
| Carbon monoxide | 0.2 | 66 |

The design basis is 5064 lb/h of nitrocyclohexane produced in the reactor. The process is carried out in essentially the same manufacturing setup used for propane nitration in Example 1, except for the addition of a condenser and a flash pot after the absorber, and two separators after the first stripping apparatus.

The reaction product stream 304 is cooled in a first condenser 305 to produce a condensed reaction product stream 306, which enters a three-phase flash vessel 307. The three-phase flash vessel 307 performs a three phase (vapor-liquid-liquid) flash/quench of the condensed reaction product stream 306 and produces a gas phase 308 and two distinct liquid phases—an oil phase 309 (including nitroalkanes) and an aqueous phase 310 (including water and organic acids). The oil phase 309 and the aqueous phase 310 segregate much better than the oil phase 209 and the aqueous phase 210 in the propane nitration in Example 1, principally because of the greater hydrophobicity of cyclohexane and a considerable density difference with water ($\rho=0.8$ g/cc).

Using an aqueous phase recycle as a diluent for nitric acid may not work for the nitration of cyclohexane as it does for the nitration of propane due to the solubility limits of adipic acid in water—which may lead to an acid precipitate. Thus, in this case the entire aqueous phase 310 is fed into an absorber 311. The oil phase 309, the aqueous phase 310, and the gas phase 308 are introduced into the absorber 311. The absorber 311 absorbs water-soluble and oil soluble components from the gas phase 308 into the oil phase 309 and into the aqueous phase 310 to form a hydrocarbon gas stream 312 and a first gas-recovered mixture 313. In the absorber 311, the aqueous phase 310 and the oil phase 309 are steam stripped with steam 314 of all non-condensable gases.

The resulting hydrocarbon gas stream 312 enters a second condenser 315 to produce a condensed hydrocarbon gas stream 316. The condensed hydrocarbon gas stream enters a flash pot 317 to produce a first top product 318, containing product off-gases, and a first bottom product 319, containing condensed cyclohexane. The first top product 318 is routed to a nitric acid recovery section. The first bottom product 319 combines with the first gas-recovered mixture 313, which primarily contains unreacted cyclohexane, nitrocyclohexane, water, cyclohexanol, adipic acid and succinic acid, to produce a second gas-recovered mixture 320, which is phase-separated in a separator 321 into a gas-recovered aqueous phase 322 and a gas-recovered oil phase 323. During separation some of the diacids are washed out of the second gas-recovered mixture 320 due to their hydrophilic nature.

In alternative embodiments, the oil phase 309 and the aqueous phase 310 do not enter the absorber 311 and instead directly enter the separator 321. In such alternative embodiments, the first gas-recovered mixture 313 may enter a stripping apparatus for removing dissolved organic compounds prior to combining with the first bottom product 319 to produce a second gas-recovered mixture 320. The second gas-recovered mixture may then enter the separator 321, where a combined gas-recovered aqueous phase and a combined gas-recovered oil phase may be formed from the stripped gas-recovered mixture, the oil phase 309, and the aqueous phase 310. For example, water-soluble portions of the stripped gas-recovered mixture may combine with the aqueous phase 310 to form the combined gas-recovered aqueous phase and oil soluble portions of the stripped gas-recovered mixture may combine with the condensed oil phase 309 to form the combined gas-recovered oil phase.

In the case of propane nitration, a considerable amount of 2-nitropropane entrains in the gas-recovered aqueous phase 322 (1.7%/304 lb/h); however in this case the gas-recovered aqueous phase 322 from the separator 321 contains a negligible amount (500 ppm/3:9 lb/h) of the product nitrocyclohexane. Therefore, this gas-recovered aqueous phase 322 is sent directly to a water treatment section. Nitrocyclohexanes are recovered in a recovery system from the gas-recovered oil phase 323. The gas-recovered oil phase 323 contains unreacted cyclohexane in addition to the nitroalkanes and organic acids and is directly sent to a neutralization section.

Sodium bicarbonate 324 is added to the gas-recovered oil phase 323 in a mixer 325, resulting in a first neutralized oil stream 326 containing the water-soluble sodium salts of adipic and succinic acid. The first neutralized oil stream 326 is then routed to a neutralization tank 327, which is agitated to allow for thorough mixing and degassing of carbon-dioxide released during neutralization. A second neutralized oil stream 328 exits the neutralization tank 327. Carbon-dioxide 329 is vented from the neutralization tank 327 and the second neutralized oil stream 328 (containing water-soluble salts) is sent to a Karr® column 330 for washing off the dissolved salts with deionized water 331 to form a washed oil stream 332 and a washed aqueous stream 333, which is routed to a waste water section. The washed oil stream 332 is then sent to a first stripping apparatus 334. The first stripping apparatus 334 divides the washed oil stream 332 into a second top product 335 and a second bottom product 336. Water 337 is added to azeotropically distill cyclohexane and cyclohexanol at the second top product 335 and high-boiling nitrocyclohexane is obtained in the second bottom product 336. The second top product 335 enters a third condenser 338 to produce a condensed second top product 339, which then enters a second separator 340 to produce an aqueous stream 341, which is sent to a water treatment section, and a first oil stream 342, which includes unreacted cyclohexane and some nitrocyclohexane. The first oil stream 342 is recycled back to a recycling system 343, where the first oil stream 342 is combined with the hydrocarbon feedstock 301.

The second bottom product 336 contains cyclohexanol, nitrocyclohexanol, heavies (such as nitroalcohols and dinitro compounds) and water. The second bottom product 336 enters a fourth condenser 344 to produce a condensed second bottom product 345, which then enters a third separator 346. The third separator 346 separates the condensed second bottom product 345 into a second aqueous stream 347 and a second oil stream 348. The second oil stream 348 is routed to a Nitroalkane Recovery Section (NRS) 349. The second aqueous stream 347 is sent to a water treatment section.

The NRS includes two columns, a Combiner Drying-Volatile Removal column (CDVR) 350 and a nitrocyclohexane column 351. The oil stream 348 enters the CDVR 350 and water and cyclohexanol exit the CDVR 350 in a CDVR top product 352. A CDVR bottom product 353 essentially contains nitrocyclohexane and heavies (such as nitroalcohols and dinitro compounds). The CDVR bottom product 353 is sent to the nitrocyclohexane column 351, which essentially recovers essentially pure nitrocyclohexane in a first nitroalkane stream 354 and heavies (such as nitroalcohols and dinitro compounds) in a nitrocyclohexane column'bottom product 355.

Thus, the addition of relatively simple equipment (three condensers (315, 338, and 344), a flash pot (317), and two separators (340 and 346)) to the 2-nitropropane process, along with the bypass of certain sections, enables the manufacture of nitrocyclohexane in essentially the same production facility used for 2-nitropropane.

Example 3

Nitration of Isobutane

Tert-nitrobutane is a potentially useful molecule that can be readily synthesized by high pressure nitration. Nitration of isobutane by high pressure nitration results in the formation of tert-nitrobutane with a selectivity of approximately 96%. The main nitrated byproducts are isomers of 1-nitro, 2-methylpropane. High nitric acid conversion (>95%) and isobutane conversion ranges from about 10 to 30% can be achieved.

The gaseous byproducts from the reaction are the usual nitration off-gases: $CO$, $CO_2$, $N_2$, $N_2O$, and $NO$, in addition to liquid byproducts, which include nitroalcohols, nitro compounds, and oxidation byproducts such as tert-nitrobutane; 2-nitrobutane; 1-nitro, 2-methylpropane (an isomer of tert-nitrobutane); 2-nitro, 2-methyl, 1-propanol (NMP); 1-nitro, 2-methyl,2-propanol; 1,2-dinitro,2-methyl propane, and acetic acid. In the laboratory, the liquid nitration product is readily phase separated into hydrocarbon and aqueous phases in a separatory funnel. The hydrocarbon phase is neutralized using deionized water and sodium bicarbonate and the mixture is readily separated.

Figure 4:
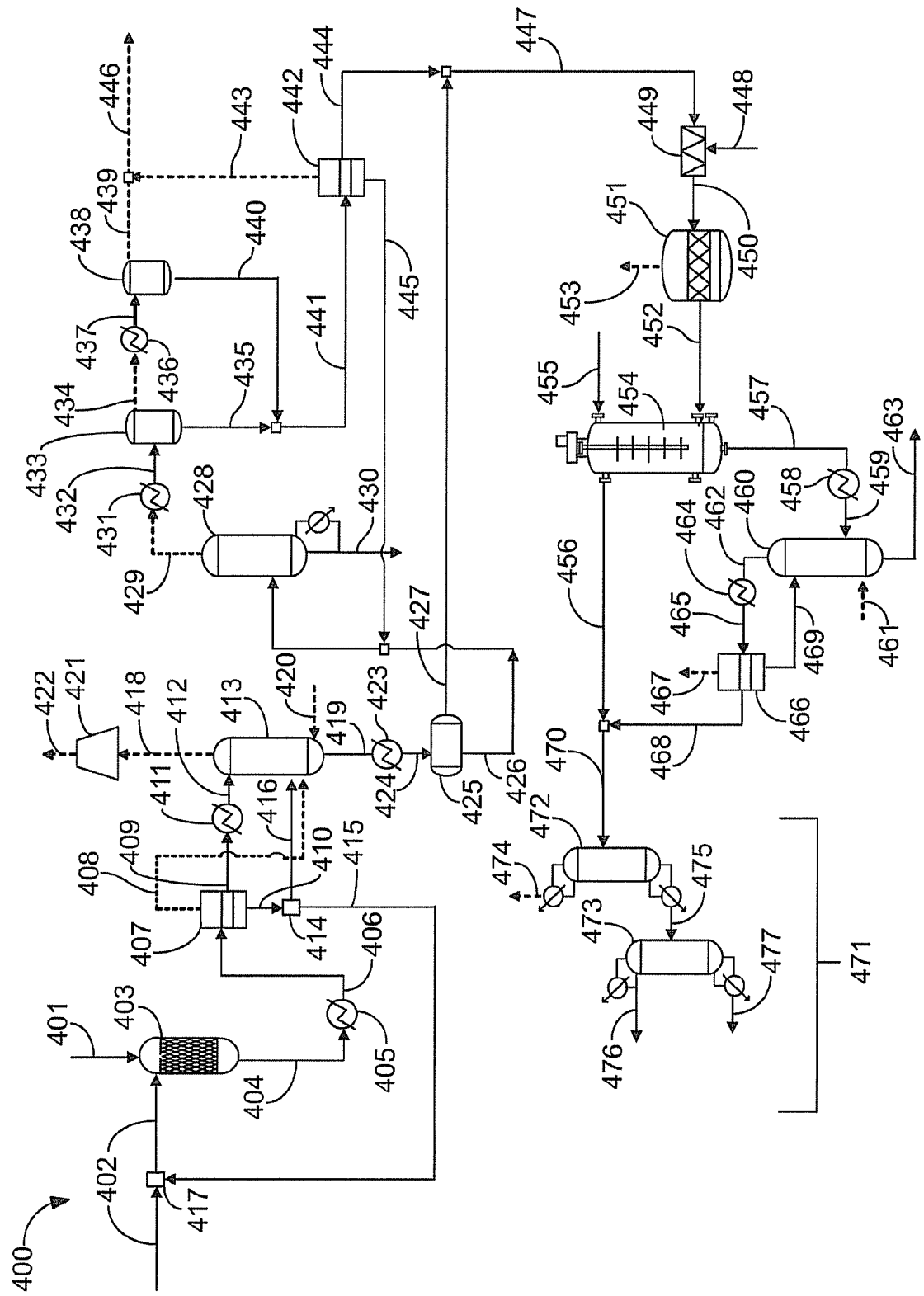
FIG. 4 is a schematic diagram of an apparatus for synthesizing tert-nitrobutane, in accordance with an illustrative embodiment.

Isobutane is nitrated using about 30 weight percent dilute aqueous nitric acid as the nitrating agent at the following process conditions: about 1200 psig reactor pressure, about 210 degrees Celsius reactor temperature, a residence time of about 120 seconds, and an isobutane to nitric acid mole ratio of about 1.3:1. FIG. 4 illustrates an apparatus 400 for synthesizing tert-nitrobutane. A hydrocarbon feedstock 401, comprising isobutane, and aqueous nitric acid 402 are introduced into a reactor 403 and react to form a reaction product stream 404. A composition of a typical reaction product stream 404 from the reactor 403 is summarized in Table 3.

TABLE 3

Reactor product stream composition for isobutane nitration

| Component | Weight percent | lb/h |
|---|---|---|
| Isobutane | 13.8 | 9860 |
| Nitric acid | 0.8 | 537 |
| Water | 69.4 | 49620 |
| Tert-nitrobutane | 7.1 | 5064 |
| 2-nitrobutane | 0.3 | 179 |
| 1-nitro, 2-methyl propane | 0.2 | 145 |
| 1-nitro, 2-methyl, 2-propanol | 0.3 | 202 |
| 2-nitro, 2-methyl propanol | 1.4 | 998 |
| 1,2-dinitro, 2-methyl propane | 1.2 | 882 |
| Acetic acid | 1.4 | 982 |
| Nitric oxide | 1.4 | 1027 |
| Nitrous oxide | 0.5 | 333 |
| Nitrogen | 0.4 | 317 |

TABLE 3-continued

Reactor product stream composition for isobutane nitration

| Component | Weight percent | lb/h |
|---|---|---|
| Carbon monoxide | 0.3 | 191 |
| Carbon dioxide | 1.6 | 1117 |

A conceptual process flow scheme is designed, based on laboratory studies, so that tert-nitrobutane is manufactured in the same manufacturing set-up used in Examples 1 and 2 for propane and cyclohexane nitration. The design basis is 5064 lb/h of tert-nitrobutane produced in the reactor 403.

The reaction product stream 404 is cooled in a first condenser 405 to produce a condensed reaction product stream 406, which enters a first three-phase flash vessel 407. The first three-phase flash vessel 407 performs a three phase (vapor-liquid-liquid) flash/quench of the condensed reaction product stream 406 and produces a gas phase 408, including NO, $N_2O$, $N_2$, CO, and $CO_2$, and two distinct liquid phases—an oil phase 409 (including nitroalkanes) and an aqueous phase 410 (including water and organic acids). The oil phase 409 is cooled to between about 10 and 20 degrees Celsius in a second condenser 411 to produce a condensed oil phase 412 to reduce loss of tert-nitrobutane in the overhead. The condensed oil phase 412 is introduced into an absorber 413. The aqueous phase 410 enters a stream-splitter 414, which splits the aqueous phase 410 into a first aqueous stream 415 and a second aqueous stream 416. The stream-splitter 414 may include at least one flow-meter to control the amount of the aqueous phase 410 in the first aqueous stream 415 and the second aqueous stream 416. The first aqueous stream 415 enters a recycling system 417. The recycling system 417 mixes the first aqueous stream 415 with the aqueous nitric acid 402 such that the first aqueous stream 415 dilutes the aqueous nitric acid 402 prior to entering the reactor 403.

Preferably, 70-80% of the aqueous phase 410 coming out of the post-reactor first three-phase flash vessel 407 is recycled to the reactor 403 as nitric acid diluent. Nitroalkanes typically have low solubility in water, moreover nitroalkanes are significantly less reactive than alkanes and therefore their presence in the reactor should not affect reactor performance significantly.

The absorber 413 absorbs water-soluble and oil soluble components from the gas phase 408 into the oil phase 409 and into the second aqueous stream 416 to form a hydrocarbon gas stream 418 and a gas-recovered mixture 419. In the absorber 413, the gas phase 408 is steam stripped with steam 420 of all volatiles at about 41-74 psi (3-5 atm) and the resulting hydrocarbon gas stream 418, which essentially contains un-reacted isobutane and gas byproducts, is then compressed to about 147 psi (10 atm) in a two-stage compressor 421 before a compressed hydrocarbon gas stream 422 is sent to isobutane recovery. The gas-recovered mixture 419 from the absorber 413 is cooled in a third condenser 423 to produce a condensed gas-recovered mixture 424, which is phase-separated in a separator 425 into a gas-recovered aqueous phase 426 and a gas-recovered oil phase 427. Unlike the nitration of other hydrocarbons, such as propane, cyclohexane, and n-octane, the nitration of isobutane forms undesired heavy nitroalkanols (1-nitro,2-methyl,2-propanol and 2-nitro,2-methyl,2-propanol), which remain in the gas-recovered aqueous phase 426 along with byproduct organic acid and unreacted nitric acid. Tert-nitrobunanes are recovered in a recovery system from both the gas-recovered aqueous phase 426 and the gas-recovered oil phase 427.

In alternative embodiments, the condensed oil phase 412 and the second aqueous stream 416 do not enter the absorber 413 and instead directly enter the separator 425. In such alternative embodiments, the condensed gas-recovered mixture 424 may enter a stripping apparatus for removing dissolved organic compounds prior to entering the separator 425. In the separator 425, a combined gas-recovered aqueous phase and a combined gas-recovered oil phase may be formed from the stripped gas-recovered mixture, the condensed oil phase 412, and the second aqueous stream 416. For example, water-soluble portions of the stripped gas-recovered mixture may combine with the second aqueous stream 416 to form the combined gas-recovered aqueous phase and oil soluble portions of the stripped gas-recovered mixture may combine with the condensed oil phase 412 to form the combined gas-recovered oil phase.

The gas-recovered aqueous phase 426 is further sent to a first stripping apparatus 428, which is operated at atmospheric pressure to recover dissolved tert-nitrobutane. The first stripping apparatus 428 divides the gas-recovered aqueous stream 426 into a first top product 429 and a first bottom product 430, which is sent to a water treatment section. Water, organic acids, and nitric acid are obtained as the first bottom product 430, whereas the first top product 429 is cooled and separated to obtain tert-nitrobutane.

The first top product 429 is introduced into a fourth condenser 431 to produce a condensed first top product 432, which is introduced into a first flash pot 433 to provide a second top product 434 and a second bottom product 435. The second top product 434 is then introduced into a fifth condenser 436 to produce a condensed second top product 437, which is then introduced into a second flash pot 438 to provide a third top product 439 and a third bottom product 440. The second bottom product 435 and the third bottom product 440 are combined to form a fourth bottom product 441. The fourth bottom product 441 enters a second three-phase flash vessel 442 to produce a fourth top product 443, a middle product 444, which is predominantly an oil phase, and a fifth bottom product 445, which is predominantly aqueous phase. The fifth bottom product 445 is recycled back to the gas-recovered aqueous phase 426. The fourth top product 443 combines with the third top product 439 to form a non-condensable stream 446.

The middle product 444 combines with the gas-recovered oil phase 427 to produce a first oil stream 447. The first oil stream 447 contains the recovered tert-nitrobutane, along with dissolved organic acids, which may need to be removed. Sodium bicarbonate 448 is added to the first oil stream 447 in a mixer 449, resulting in a first neutralized oil stream 450. The first neutralized oil stream 450 is then routed to a neutralization tank 451, which is agitated to allow for thorough mixing and degassing of carbon-dioxide released during neutralization. A second neutralized oil stream 452 exits the neutralization tank 451. Carbon-dioxide 453 is vented from the neutralization tank 451 and the second neutralized oil stream 452 (containing dissolved salts of acetic acid) is sent to a Karr® column 454 for washing off the dissolved salts with deionized water 455 to form a washed oil stream 456 and a washed aqueous stream 457. A reciprocating Karr® column is known to be an effective mass transfer device. The washed aqueous stream 457 from the Karr® column 454 contains dissolved tert-nitrobutane and some heavy nitroalkanols, which are condensed in a sixth condenser 458 to produce a condensed washed aqueous stream 459, which is sent to a second stripping apparatus 460 to be stripped with steam 461. The second stripping apparatus 460 divides the condensed washed aqueous stream 459 into a fifth top product 462 and a sixth bottom product 463, which is sent to a waste water section. The fifth top product 462 enters a seventh condenser 464, to produce a condensed fifth top product 465. The condensed fifth top product 465 enters a third three-phase flash vessel 466, which separates the condensed fifth top product 465 into a second gas phase 467, a second oil phase 468, and a second aqueous phase 469. The second aqueous phase 469 is returned to the second stripping apparatus 460. The second oil phase 468 is combined with the washed oil stream 456 to form a second oil stream 470, which is routed to a Nitroalkane Recovery Section (NRS) 471.

The NRS consists of at least two columns, a Combiner Drying-Volatile Removal column (CDVR) 472 and a tert-nitrobutane column 473. The second oil stream 470 enters the CDVR 472. Unlike the nitration of propane and cyclohexane in Examples 1 and 2, the CDVR 472 in this case recovers the remainder of unreacted reactant (isobutane) 474 to be recycled back to the reactor 403. A CDVR bottom product 475 is sent to the tert-nitrobutane column 473, which recovers a first nitroalkane stream 476, which contains tert-nitrobutane at the desired purity specifications. A tert-nitrobutane bottom product 477 may be wasted or may be further processed to recover minor components.

Example 4

Nitration of n-octane

Nitration of n-octane by high pressure nitration results in the formation of nitro-n-octanes. High nitric acid conversion (>99%) and n-octane conversion ranges from about 53 to 56% can be achieved.

The gaseous byproducts from the reaction are the usual nitration off-gases: CO, $CO_2$, $N_2$, $N_2O$, and NO in addition to liquid byproducts, which include n-octonone, n-octanol, acetic acid, propionic acid, butyric acid, pentanoic acid, and low volatility heavies (such as nitroalcohols and dinitro compounds). During the laboratory runs, the liquid nitration product is readily phase separated into hydrocarbon and aqueous phases in a separatory funnel. The hydrocarbon phase is neutralized using deionized water and sodium bicarbonate and the mixture is readily separated (decanted).

Figure 5:
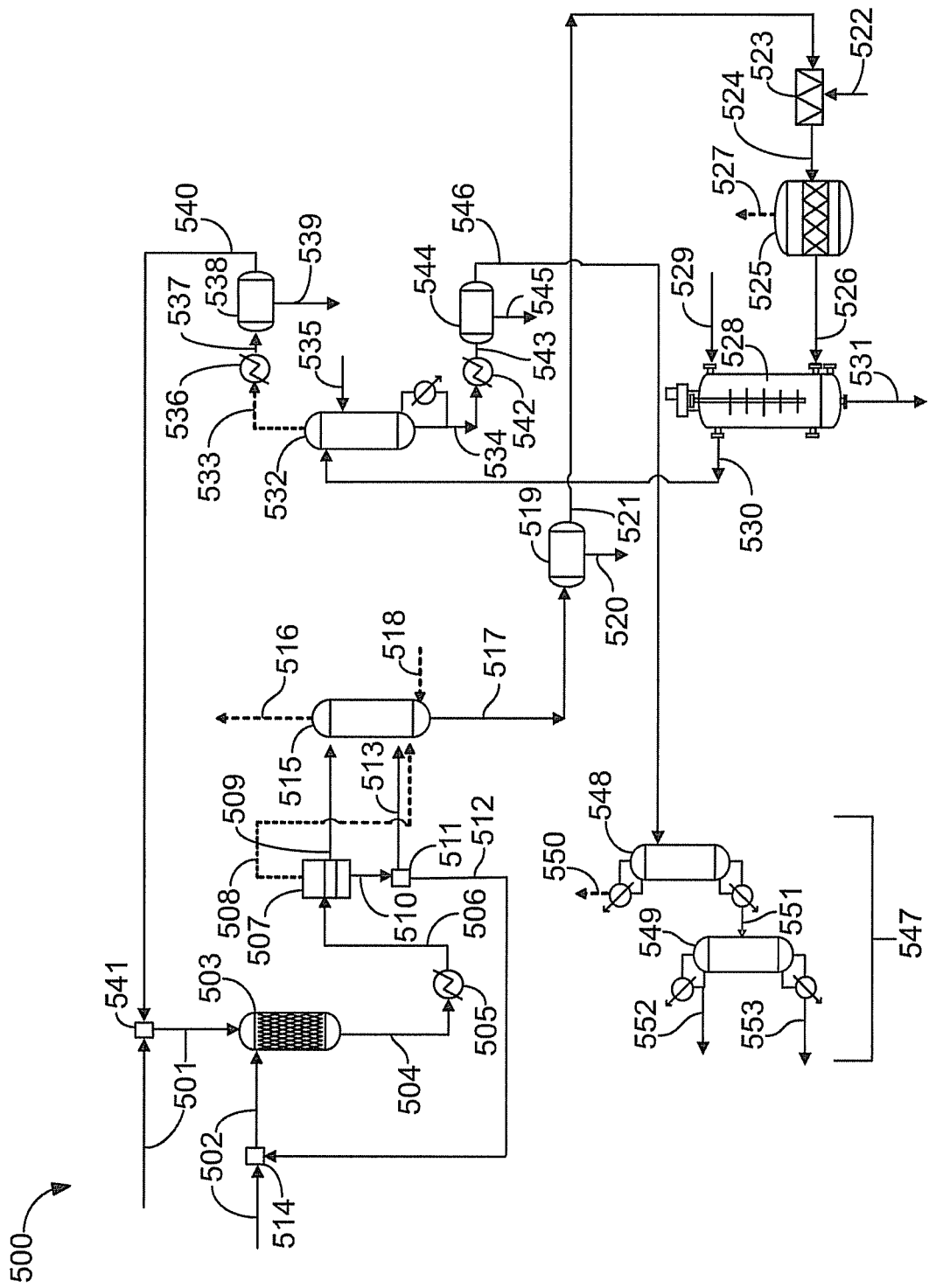
FIG. 5 is a schematic diagram of an apparatus for synthesizing nitro-n-octane, in accordance with an illustrative embodiment.

N-octane is nitrated using about 30 weight percent dilute aqueous nitric acid as the nitrating agent at the following process conditions: about 1200 psig reactor pressure, about 220 degrees Celsius reactor temperature, a residence time of about 120 seconds, and an n-octane to nitric acid mole ratio of about 1.2:1. FIG. 5 illustrates an apparatus 500 for synthesizing nitro-n-octane. A hydrocarbon feedstock 501, comprising n-octane, and aqueous nitric acid 502 are introduced into a reactor 503 and react to form a reaction product stream 504. A composition of a typical reaction product stream 504 from the reactor 503 is summarized in Table 4.

TABLE 4

Reactor product stream composition for n-octane nitration

| Component | Weight percent | lb/h |
| --- | --- | --- |
| Water | 54.4 | 13141 |
| Nitric acid | 0.0 | 7 |
| N-octane | 17.4 | 4202 |
| N-octanol | 1.7 | 406 |
| N-octanone | 0.6 | 135 |
| Nitro-n-octane | 21.0 | 5064 |
| Acetic acid | 0.8 | 200 |
| Propionic acid | 0.7 | 164 |
| Butyric acid | 0.5 | 113 |
| Pentanoic acid | 0.2 | 40 |
| Carbon dioxide | 1.0 | 244 |
| Nitrogen dioxide | 0.0 | 0 |
| Nitrous oxide | 0.6 | 134 |
| Nitric oxide | 0.1 | 15 |
| Nitrogen | 0.8 | 184 |
| Carbon monoxide | 0.4 | 86 |

A conceptual process flow scheme is designed based on laboratory studies so that nitro-n-octane is produced in the same manufacturing set-up used in Examples 1, 2, and 3. The design basis is 5064 lb/h of nitro-n-octane produced in the reactor 503. The design is similar to the design in Example 2 for cyclohexane nitration.

The reaction product stream 504 is cooled in a first condenser 505 to produce a condensed reaction product stream 506, which enters a three-phase flash vessel 507. The three-phase flash vessel 507 performs a three phase (vapor-liquid-liquid) flash/quench of the condensed reaction product stream 506 and produces a gas phase 508 and two distinct liquid phases—an oil phase 509 (including nitroalkanes) and an aqueous phase 510 (including water and organic acids). The oil and the aqueous phases segregate easily principally because of the greater hydrophobicity of n-octane and a considerable density difference with water ($\rho$=0.7 g/cc).

The aqueous phase 510 enters a stream-splitter 511, which splits the aqueous phase 510 into a first aqueous stream 512 and a second aqueous stream 513. The stream-splitter 511 may include at least one flow-meter to control the amount of the aqueous phase 510 in the first aqueous stream 512 and the second aqueous stream 513. The first aqueous stream 512 enters a recycling system 514. The recycling system 514 mixes the first aqueous stream 512 with the aqueous nitric acid 502 such that the first aqueous stream 512 dilutes the aqueous nitric acid 502 prior to entering the reactor 503.

Preferably, 70-80% of the aqueous phase 510 coming out of the post-reactor three-phase flash vessel 507 is recycled to the reactor 503 as nitric acid diluent. Nitroalkanes typically have low solubility in water. Moreover nitroalkanes are significantly less reactive than alkanes and therefore their presence in the reactor should not affect reactor performance significantly.

The oil phase 509, the second aqueous stream 513, and the gas phase 508 are introduced into an absorber 515. The absorber 515 absorbs water-soluble and oil soluble components from the gas phase 508 into the oil phase 509 and into the second aqueous stream 513 to form a hydrocarbon gas stream 516 and a gas-recovered mixture 517. In the absorber 515, the second aqueous stream 513 and the oil phase 509 are steam stripped with steam 518 of all non-condensable gases. Since little or no n-octane leaves from the top of the absorber 515, the second condenser 315 and the flash pot 317 present in Example 2 (cyclohexane nitration) are bypassed and the hydrocarbon gas stream 516, which contains product off-gases such as NO, $N_2O$, CO, $CO_2$ and contains very little n-octane, is directly sent to a nitric acid recovery section.

The gas-recovered mixture 517 is phase-separated in a separator 519 into a gas-recovered aqueous phase 520 and a gas-recovered oil phase 521. The gas-recovered aqueous phase 520 from the separator 519 contains a negligible amount (96 ppm/0.4 lb/h) of the product nitro-n-octane. Therefore, this gas-recovered aqueous phase 520 is sent directly to a water treatment section. Nitro-n-octanes are recovered in a recovery system from the gas-recovered oil phase 521. The gas-recovered oil phase 521 contains unreacted n-octane in addition to the nitroalkanes and organic acids (such as acetic acid, propanoic acid, butanoic acid, and pentanoic acid) and is directly sent to a neutralizer section.

In alternative embodiments, the oil phase 509 and the second aqueous stream 513 do not enter the absorber 515 and instead directly enter the separator 519. In such alternative embodiments, the gas-recovered mixture 517 may enter a stripping apparatus for removing dissolved organic compounds prior to entering the separator 519. In the separator 519, a combined gas-recovered aqueous phase and a combined gas-recovered oil phase may be formed from the stripped gas-recovered mixture, the oil phase 509, and the second aqueous stream 513. For example, water-soluble portions of the stripped gas-recovered mixture may combine with the second aqueous stream 513 to form the combined gas-recovered aqueous phase and oil soluble portions of the stripped gas-recovered mixture may combine with the oil phase 509 to form the combined gas-recovered oil phase.

Sodium bicarbonate 522 is added to the gas-recovered oil phase 521 in a mixer 523, resulting in a first neutralized oil stream 524. The first neutralized oil stream 524 is then routed to a neutralization tank 525, which is agitated to allow for thorough mixing and degassing of carbon-dioxide released during neutralization. A second neutralized oil stream 526 exits the neutralization tank 525. Carbon-dioxide 527 is vented from the neutralization tank 525 and the second neutralized oil stream 526 (containing dissolved salts) is sent to a Karr® column 528 for washing off the dissolved salts with deionized water 529 to form a washed oil stream 530 and a washed aqueous stream 531, which is sent to a waste water section. The washed oil stream 530 is then sent to a first stripping apparatus 532. The first stripping apparatus 532 divides the washed oil stream 530 into a top product 533 and a bottom product 534. Water 535 is added to azeotropically distill n-octane, n-octanol, and n-octanone at the top product 533 and high-boiling nitro-n-octane is obtained in the bottom product 534. The top product 533 enters a second condenser 536 to produce a condensed top product 537, which then enters a second separator 538 to produce a third aqueous stream 539, which is essentially water, and a first oil stream 540, which includes unreacted n-octane (along with n-octanol, n-octanone, and some nitro-n-octane). The third aqueous stream 539 is sent to a water treatment section. The first oil stream 540 is recycled back to a recycling system 541, where the first oil stream 540 is combined with the hydrocarbon feedstock 501.

The bottom product 534 contains n-octanol, nitro-n-octane, heavies (such as nitroalcohols and dinitro compounds), and water. The bottom product 534 enters a third condenser 542 to produce a condensed bottom product 543, which then enters a third separator 544. The third separator 544 separates the condensed first bottom product 543 into a fourth aqueous stream 545 and a second oil stream 546. The fourth aqueous stream 545 is sent to a water treatment section. The second oil stream 546 is routed to a Nitroalkane Recovery Section (NRS) 547.

The NRS consists of two columns, a Combiner Drying-Volatile Removal column (CDVR) 548 and a nitro-n-octane column 549. The oil stream 546 enters the CDVR 548 and water, n-octanol, and n-octanone exit the CDVR 548 in a CDVR top product 550. A CDVR bottom product 551 essentially contains nitro-n-octane and heavies (such as nitroalcohols and dinitro compounds). The CDVR bottom product 551 is sent to the nitro-n-octane column 549, which essentially recovers essentially pure nitro-n-octane in a first nitroalkane stream 552 and heavies (such as nitroalcohols and dinitro compounds) in a nitro-n-octane column bottom product 553.

SUMMARY OF EXAMPLES

Examples 1-4 show a designed downstream process scheme lies with feed-flexibility to operate the manufacturing unit for nitration of at least four different feedstocks, such as propane, isobutane, cyclohexane, and n-octane. Tables 5 and 6 below show the hydrodynamic characteristics of the absorber (shown as 213, 311, 413, and 515) and the first stripping apparatus (shown as 228, 334, 428, and 532) for the four alkane nitration cases discussed above in Examples 1, 2, 3, and 4. The absorber and first stripping apparatus can be packed columns sized at 2.25-2.4 feet and 2.20-3.32 feet diameter respectively in the simplest case of randomly filled packing. The parameters that may determine efficient operation of a packed column are the maximum fractional capacity and pressure drop/foot of column length. Typically, industrially operated packed columns are designed to operate at a maximum fractional capacity of 70-80% and pressure drop of up to 1 inch-water/foot of column length. While the optimal column diameters vary depending on the hydrocarbon to be nitrated, the largest column diameter (2.4 feet for the absorber and 3.32 feet for the first stripping apparatus) may be used, allowing for the same equipment for the nitration of different hydrocarbons and thus, a feed-flexible nitration plant design.

TABLE 5

Hydrodynamic characteristics of absorber column

| Alkane | Column diameter (feet) | Packing type | Packing size (inches) | Maximum fractional capacity | Pressure drop (inch-water/foot) |
|---|---|---|---|---|---|
| Propane | 2.4 | Raschig (Ceramic) | 1.5 | 0.750 | 0.351 |
| Isobutane | 2.4 | Raschig (Ceramic) | 1.5 | 0.800 | 0.988 |
| Cyclohexane | 2.25 | Raschig (Ceramic) | 1.5 | 0.700 | 0.111 |
| N-octane | 2.25 | Raschig (Ceramic) | 1.5 | 0.500 | 0.042 |

TABLE 6

Hydrodynamic characteristics of first stripping apparatus column

| Alkane | Column diameter (feet) | Packing type | Packing size (inches) | Maximum fractional capacity | Pressure drop (inch-water/foot) |
|---|---|---|---|---|---|
| Propane | 2.20 | Raschig (Ceramic) | 3 | 0.500 | 0.272 |
| Isobutane | 2.20 | Raschig (Ceramic) | 3 | 0.500 | 0.230 |
| Cyclohexane | 2.73 | Raschig (Ceramic) | 3 | 0.500 | 0.282 |
| N-octane | 3.32 | Raschig (Ceramic) | 3 | 0.850 | 0.929 |

While the invention has been described above according to its preferred embodiments, it can be modified within the spirit and scope of this disclosure. This application is therefore intended to cover any variations, uses, or adaptations of the invention using the general principles disclosed herein. Further, the application is intended to cover such departures from the present disclosure as come within the known or customary practice in the art to which this invention pertains and which fall within the limits of the following claims.

What is claimed is:

1. A process for synthesizing a first nitroalkane and a second nitroalkane, the process comprising:
    reacting a first feedstock in a reactor with aqueous nitric acid at a reaction temperature of between about 140 degrees Celsius and about 325 degrees Celsius and a reaction pressure of at least about $6.89 \times 10^6$ Pascal to produce a first reaction product stream;
    quenching the first reaction product stream in a cooling system such that the first reaction product stream phase separates into at least a first gas phase, a first oil phase, and a first aqueous phase;
    absorbing in an absorber water-soluble and oil-soluble components from the first gas phase to form a first hydrocarbon gas stream and a first gas-recovered mixture;
    forming in a separator a first combined gas-recovered aqueous phase and a first combined gas-recovered oil phase from the first gas-recovered mixture, the first oil phase, and the first aqueous phase;
    recovering the first nitroalkane from at least one of the first combined gas-recovered aqueous phase and the first combined gas-recovered oil phase;
    reacting a second feedstock in the reactor with aqueous nitric acid at a reaction temperature of between about 140 degrees Celsius and about 325 degrees Celsius and a reaction pressure of at least about $6.89 \times 10^6$ Pascal to produce a second reaction product stream;
    quenching the second reaction product stream in the cooling system such that the second reaction product stream phase separates into at least a second gas phase, a second oil phase, and a second aqueous phase;
    absorbing in the absorber water-soluble and oil-soluble components from the second gas phase to form a second hydrocarbon gas stream and a second gas-recovered mixture;
    forming in the separator a second combined gas-recovered aqueous phase and a second combined gas-recovered oil phase from the second gas-recovered mixture, the second oil phase, and the second aqueous phase; and
    recovering the second nitroalkane from at least one of the second combined gas-recovered aqueous phase and the second combined gas-recovered oil phase.

2. A process according to claim 1, wherein the first nitroalkane and the second nitroalkane are recovered in a recovery system.

3. A process according to claim 2, wherein the recovery system comprises at least one stripping apparatus.

4. A process according to claim 1, wherein the first feedstock comprises propane, and wherein the first nitroalkane is 2-nitropropane.

5. A process according to claim 4, wherein the second feedstock comprises isobutane, and wherein the second nitroalkane is tert-nitrobutane.

6. A process according to claim 1, wherein first feedstock comprises cyclohexane, and wherein the first nitroalkane is nitrocyclohexane.

7. A process according to claim 6, wherein the second feedstock comprises n-octane, and wherein the second nitroalkane is nitro-n-octane.

\* \* \* \* \*